United States Patent [19]
Liu

[11] Patent Number: 5,416,879
[45] Date of Patent: May 16, 1995

[54] APPARATUS AND METHOD FOR MEASURING LIGHT ABSORPTION IN SMALL AQUEOUS FLUID SAMPLES

[75] Inventor: Su Y. Liu, Sarasota, Fla.

[73] Assignee: World Precision Instruments, Inc., Sarasota, Fla.

[21] Appl. No.: 169,310

[22] Filed: Dec. 17, 1993

Related U.S. Application Data

[63] Continuation-in-part of Ser. No. 38,520, Mar. 29, 1993, abandoned.

[51] Int. Cl.$^6$ .............................................. G02B 6/20
[52] U.S. Cl. ..................................... 385/125; 385/12; 385/13
[58] Field of Search ................ 385/12, 13, 123, 125, 385/126, 39

[56] References Cited

U.S. PATENT DOCUMENTS

| | | | |
|---|---|---|---|
| 3,894,788 | 7/1975 | Gambling et al. | 385/125 |
| 4,045,119 | 8/1977 | Eastgate | 385/125 |
| 5,165,773 | 11/1992 | Nath | 385/125 |
| 5,244,813 | 9/1993 | Walt et al. | 385/12 X |

FOREIGN PATENT DOCUMENTS 2719504  11/1978  Germany ........................... 385/125

OTHER PUBLICATIONS

"Ultra–Sensitive UV Detection in Micro Separation", Journal of High Resolution Chromotography, 1989, J. P. Chervet et al, pp. 278–281 no month available.
"Micropipette Adaptor for Spectrophotometers", Rev. Sci. Instrum. 61 (5), May 1990, H. R. Garner et al, pp. 1433–1435.

*Primary Examiner*—Rodney B. Bovernick
*Assistant Examiner*—Hemang Sanghavi
*Attorney, Agent, or Firm*—Chilton, Alix & Van Kirk

[57] ABSTRACT

Water or some other aqueous fluid is employed as the light transmitting medium of a liquid-core fiber-optic wave guide employed as a spectrophotometer cell by employing, to define the core region, a polymer having a refractive index of less than 1.33. The light conducting channel defined by the aqueous fluid filled core may be a capillary or other suitably shaped vessel. The analysis of samples is accomplished by drawing a sample into the wave guide core region throughout the use of a fiber optic piston and thereafter delivering measurement light to the sample via the piston.

9 Claims, 3 Drawing Sheets

APPARATUS AND METHOD FOR MEASURING LIGHT ABSORPTION IN SMALL AQUEOUS FLUID SAMPLES

CROSS-REFERENCE TO RELATED APPLICATIONS

This application is a continuation-in-part of application Ser. No. 038,520, filed Mar. 29, 1993, now abandoned.

BACKGROUND OF THE INVENTION

1. Field of the Invention

The present invention relates to the use of water or some other aqueous liquid as the light conducting core medium of an elongated, rigid, small diameter vessel employed for light transmission. More particularly, this invention is directed to rigid tubular light guides suitable for spectrophotometric applications, and to methods of and apparatus for measuring the absorption of light in small volume aqueous fluid samples with the use of such light guides. Accordingly, the general objects of the present invention are to provide novel and improved methods and apparatus of such character.

2. Description of the Prior Art

While not limited thereto in its utility, the present invention has applicability to the field of fiber optics. Liquid core fiber-optic wave guides, i.e., light guide fibers in the form of a capillary filled with a fluid which functions as the light transmitting core, have previously been proposed. For an example of such a prior liquid-core fiber-optic wave guide, reference may be had to U.S. Pat. No. 3,894,788. Since light cannot be efficiently propagated through a fluid filled capillary unless the refractive index of the capillary is less than that of the core fluid, the wave guides of U.S. Pat. No. 3,894,788 use an organic fluid as the core liquid. These organic fluids are specially selected so as to have refractive indices which are greater than that of the particular material from which the capillary is fabricated in order to permit long distance propagation of light waves through the core liquid.

There has been a long standing desire to employ water or some other aqueous fluid in a liquid-core fiber-optic environment for the purpose of facilitating chemical analyses of aqueous solutions by light interactive processes such as light absorption, colorimetry and fluorescence. However, consistent with the teachings of U.S. Pat. No. 3,894,788, it has previously been universally believed that the low index of refraction of water and other aqueous liquids rendered it impossible to employ such materials as the light conducting core medium of a liquid-core, fiber-optic wave guide or the like.

A variety of techniques are available for use in the analysis of fluid samples. These techniques include optical methodology, particularly photometry and spectrophotometry, wherein the composition and concentration of dissolved substances are determined by measuring the absorption of light in a liquid which includes such substances. These optical analysis techniques are based on the fact that different substances will absorb light at different wave lengths. In the practice of these optical techniques, light absorption at discrete wave lengths or over a broad light spectrum, including ultraviolet, visible or infrared spectra, may be measured.

The need for instruments capable of the optical analysis of aqueous samples in the sub-milliliter volume range has grown in recent years. An important reason for this growing need is the fact that protein and DNA samples are usually in small volume aqueous samples. For example, it is often difficult to obtain large amounts of animal, especially human, tissue samples which must be analyzed. It is also costly to synthesize or purify protein, enzyme, antibody and DNA samples in large amounts.

Conventional absorption spectrometers are not sufficiently sensitive to analyze solutions prepared from the very small volume samples discussed above. For example, the approximate detection limit, defined as the lowest concentration that can be distinguished from background signal for double stranded DNA using absorption at a wave length of 260 nm is about 250 nanograms for a 0.5 ml, 10 mm light path length cuvette.

There have been efforts to reduce the requisite sample cuvette volume. Such efforts have often been characterized by a reduction in the light path length which, in turn, reduces instrument sensitivity. The smallest commercially available fluid sample cuvettes with 10 mm long light paths contain fluid volume in the 30 ul to 50 ul range. For a 5 ul volume cell, however, the path length would be limited to 0.5 mm and thus unsatisfactory for analysis.

SUMMARY OF THE INVENTION

The present invention overcomes the above-briefly discussed and other deficiencies and disadvantages of prior art liquid-core, fiber-optic wave guides. In doing so, the present invention provides a spectrophotometer cell in the form of a rigid aqueous liquid filled capillary, or other suitably shaped inflexible vessel, which may be filled with an aqueous liquid.

In accordance with a preferred embodiment of the present invention, a suitably shaped vessel, i.e., a rigid wave guide, is fabricated from an amorphous polymer material characterized by a refractive index which is lower than that of water. An example of such a material is fluorocarbon, solid at normal ambient temperatures, which has a refractive index less than 1.33. The resulting vessel will be of tubular construction and will be inflexible under the normal conditions of use to be described. Alternatively, a rigid capillary comprised of glass or other similar material may be employed and its inner wall clad with the low refractive index polymer.

The present invention also overcomes the above-briefly discussed and other deficiencies and disadvantages of the prior art liquid sample analysis techniques by providing a novel method which employs, as the sample cuvette, an axially illuminated, rigid, aqueous fluid core wave guide, of the type described above, into which the sample is drawn.

A measuring instrument in accordance with the present invention includes a spectrophotometer cell or cuvette, of the type described above, having an effective light path in the contained liquid sample that is up to a hundred times longer than that of the spectrophotometer cells presently used in this art. Light collecting efficiency is maximized by directly interfacing the fluid core wave guide with fiber optics. The requisite light path length through the sample is achieved by passing the measurement light through the sample a multiple number of times, typically twice. The combination of small volume, relatively long light path length in the sample, and high efficiency of light collection improves the absorption detection limit by at least 2 to 4 orders of magnitude in terms of the total amount of analyte required. By eliminating expensive optical and mechanical components, such as lenses and in some cases also mirrors, the end cost of an instrument embodying the present invention is reduced significantly as compared to previously available absorption photometers and spectrophotometers.

In apparatus for measuring light absorption in small aqueous fluid samples in accordance with the present invention, the rigid aqueous fluid core wave guide is optically coupled to a light source and to a means for analyzing the light, for example a photometer or a spectrophotometer, by means of optical fibers. Small volume samples are drawn into and expelled from the wave guide by means of a piston or plunger which comprises part of the aforementioned coupling optical fibers. Light is transmitted from the light source axially into a first end of the sample, i.e., the liquid core region of the wave guide, via the fiber optic piston. The wave guide confines the light to the sample in the wave guide core region. The capillary configuration of the wave guide is such that the wave guide maximizes the effective length of the light path for any given sample volume. After passing through the aqueous sample in a first direction, in a first embodiment, the light is caused to be reflected back through the sample to the fiber optic piston where it is collected and transmitted to the analysis means.

BRIEF DESCRIPTION OF THE DRAWING

The present invention may be better understood and its numerous objects and advantages will become apparent to those skilled in the art by reference to the accompanying drawings wherein like reference numerals refer to like elements in the several figures and in which.

DETAILED DESCRIPTION OF THE DISCLOSED EMBODIMENTS

Figure 1:
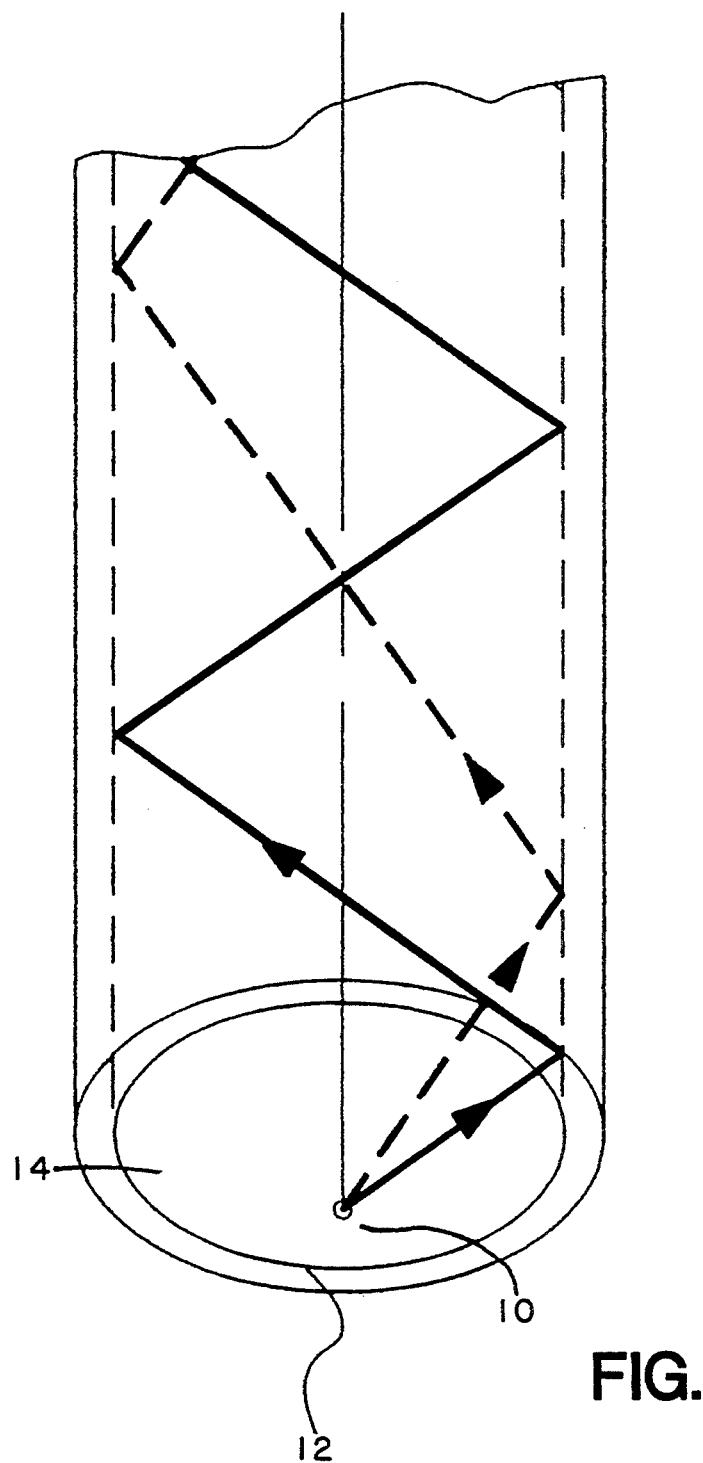
FIG. 1 is a schematic showing of a portion of an analytical cell fabricated in accordance with the present invention.
Figure 2:
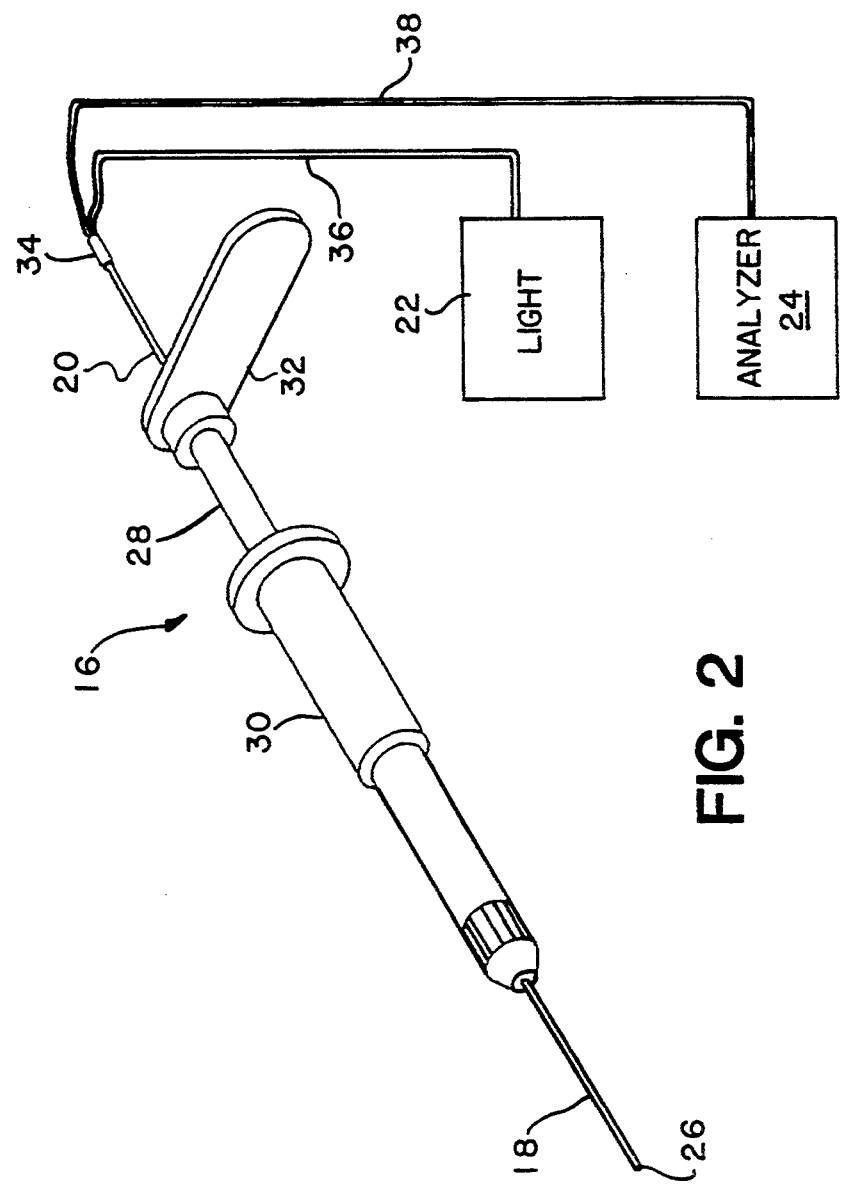
FIG. 2 is a schematic view of apparatus for measuring light absorption in small aqueous fluid samples in accordance with the invention.

In order to propagate light with negligible losses through an optical fiber, it is necessary to channel the light through a light conducting core region which is surrounded or clad by a material having a lower refractive index to the light than the material comprising the core. This arrangement results in most of the light which seeks to escape through the wall of the light conductor being reflected and, therefore, confined within the core region provided, of course, that the incident light is launched into the core material within an appropriate acceptance angle relative to the axis of the core. Most present day solid optical fibers are comprised of special silica or glass cores which are clad with thin outer coatings of silica or other materials of lesser refractive index than the core material. Solid polymer cores with cladding are also widely used. The polymer clad fibers are usually employed for relatively short distance transmission while the clad glass core fibers are typically used for longer distance light propagation.

As discussed above, the use of water as a core material has heretofore been considered impossible because of a lack of suitable materials, i.e., materials having a lower refractive index than that of water, with which to surround the water channel. The refractive index of water is approximately 1.33.

In the practice of the present invention, a rigid channel for containing a liquid core, for example a capillary, is defined through the use of a material which possesses a refractive index which is less than 1.33. Amorphous polymers with sufficiently low refractive indices can be created if their structural elements include some or all of the fluorocarbon groups $-CF_3$, $-CF_2O$, $-CF(CF_3)_2$ and $-CH(CF_3)_2$. A commercially available fluorocarbon material having a refractive index which is suitable for use in the practice of the present invention is sold by the Dupont Company under the trademark "Teflon AF". This commercially available fluorocarbon material has a refractive index in the range of approximately 1.29 to 1.31 and can be formed into rigid capillary tubing. Alternatively, the polymer may be coated on the internal wall of a suitably prepared rigid tube comprised of glass or the like thus defining an internal cladding having a refractive index of less than 1.33.

As will be described below, an external light source can be coupled to the aqueous core material of a capillary or vessel formed in accordance with the invention simply by inserting a solid optical fiber into the core fluid.

As will become apparent from the description of FIGS. 2-7 below, wave-guides in accordance with the present invention may be employed to optically analyze solutes dissolved in water by transmitting ultraviolet, visible or infrared light through the aqueous sample. The applied light beam can advance a greater distance through the analyte fluid confined in the core region of a wave guide in accordance with the invention than has been heretofore possible because most of the light which seeks to escape through the polymer or polymer-clad vessel wall is totally reflected and therefore the light is also confined within the core thus increasing the effective length of the light path through the core fluid. The increase in the light path, in turn, greatly increases the achievable sensitivity of a fluid analysis such as light absorption, colorimetry, or fluorescence because of the increased amount of light interaction with the aqueous fluid analyte.

Referring to FIG. 1, the transmitted path of light emanating from a point source 10 is the sum of the many small multiple reflections from the polymer wall 12 of the rigid capillary as the light advances through the aqueous core 14. Thus, as noted above, the effective light path through the aqueous fluid is very much longer than would be possible were it not for the present invention and, accordingly, more light energy is dissipated in the fluid than would otherwise occur. This results in greater sensitivity if light spectroscopy, light absorption or fluorimetry is performed utilizing the present invention.

A further advantage of the present invention is that it permits the analysis of minuscule amounts of liquid analyte samples because the containing capillary can have an inner diameter as small as 0.1 millimeter or less. Fluid samples with volume as little as 1 microliter or less can be directly analyzed in such small diameter capillaries by illuminating the core sample with light of appropriate wave lengths.

Referring to FIGS. 2–6, apparatus for measuring light absorption in small aqueous fluid samples is generally designated by the numeral 16. The apparatus 16 includes a rigid wave guide 18 which functions as a spectrophotometer cell, an optical fiber 20, a light source 22 and a light analyzer 24. Wave guide 18 is constructed in the same manner as the liquid-core waveguide of FIG. 1 and thus comprises a rigid capillary tube comprised of or internally coated with a material having a refractive index which is less than 1.33.

The free end 26 of wave guide 18 acts as a pipette tip into which aqueous fluid samples are drawn or expelled by employing the optical fiber 20 as a piston or plunger which is inserted into the second or upper end of the wave guide. After a sample has been drawn, the free end 26 of wave guide 18, i.e., the pipette tip, or a fluid inlet/outlet port provided therein, is sealed.

Optical fiber 20 is supported in, and passes through, a guide 28. Guide 28 is axially moveable relative to a barrel 30. Reciprocal movement is imparted to guide 28, and thus to piston/fiber 20, by means of a pusher arm 32 which is affixed to guide 28.

Optical fiber 20 is coupled to light source 22 via a coupler 34 and optical fiber 36. As noted above, the end of optical fiber 20 disposed opposite to coupler 34 is inserted in, and moveable relative to, wave guide 18 and acts as a piston. Optical fiber 20 is also coupled to light analyzer 24, i.e., a spectrophotometer, by means of coupler 34 and an optical fiber 38.

Figure 3:
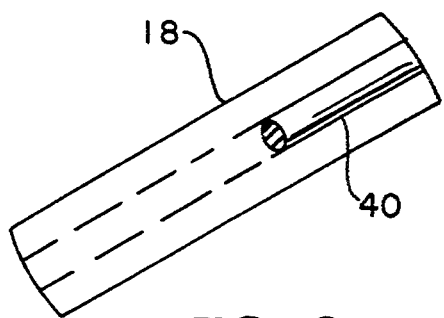
FIG. 3 is a partial enlarged view of the wave guide portion of the apparatus of FIG. 2, and FIGS. 4, 5, 6 and 7 depict alternative embodiments, on an enlarged scale, of the portion of the apparatus shown within area A of FIG. 2.

Light emitted by source 22 is transmitted to a sample 40 which has been drawn into wave guide 18 by optical fiber 20 as shown in FIG. 3. The wave guide 18 causes the received light to be propagated axially through the fluid sample 40 as shall be described below. After passing through the sample, the light is received back at optical fiber 20 and transmitted to the light analyzer 24.

Optical fiber 20 should be stiff and resistant to water and abrasion in order to function as a piston. Fiber 20 should also have the maximum obtainable ratio of core diameter to fiber outer diameter to enhance light collection. A silica core with doped silica cladding is preferred because such a construction is stiff and provides good light transmission. The cladding should be selected to enhance cable stiffness, abrasion resistance and, as noted, the maximum ratio of core/fiber diameter. Metal buffered fibers are preferred for practice of the present invention because they are thinner, stiffer, more abrasion resistant and more water resistant than alternative polymer buffered fibers. Metals commonly used for buffers in the cladding are gold, aluminum, and copper. Some of the polymer buffered fibers, e.g., polyimide, "Tefzel" and "Teflon AF", can also be used. The free end of fiber 20 can be flat or can be polished to a convex shape to minimize light loss at the fiber-fluid interface.

In accordance with the present invention, the capillary configuration of the spectrophotometer cell/wave guide 20 maximizes the light path for any given sample volume. The applied light will therefor propagate a greater distance through the sample 40 than has been heretofore possible because most of the light which seeks to escape through the polymer or polymer-clad wave guide wall is totally reflected and therefore confined within the core thus increasing the length of the light path through the sample. The increase in the light path, in turn, greatly increases the sensitivity of a fluid analysis because of the increased amount of light interaction with the aqueous fluid 40.

Figure 4:
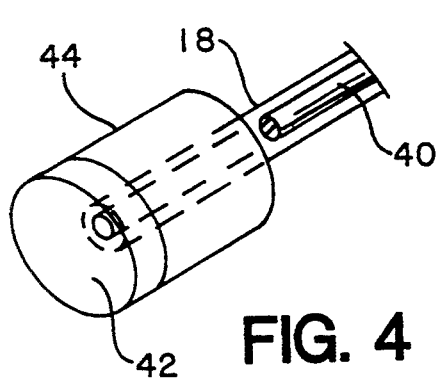

The sealing of the end of wave guide 18 is accomplished, in the embodiment shown in FIG. 4, by means of a mirror 42. Light transmitted through the sample 40 from optical fiber 18 is reflected by mirror 42 back towards fiber 18. The light path through sample 40, accordingly, is twice the length of the portion of the wave guide core which is occupied by the sample. The mirror 42 is affixed to a first end of an annular wave guide receiver 44 which fits over the wave guide 18 in the manner of a sleeve. If necessary, suitable means may be employed to ensure against leakage of the sample 40 such as, for example, providing a sealing ring on the inside of receiver 44.

Figure 5:
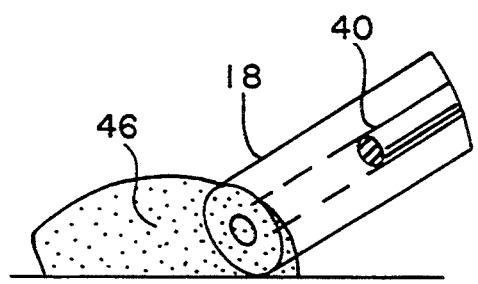

FIG. 5 depicts an alternate embodiment for the wave guide and mirror interface. In FIG. 5 the wave guide end 26 is shown as having been brought into contact with a mercury droplet 46 after the sample 40 has been drawn. The mercury droplet 46 acts as a mirror.

Figure 6:
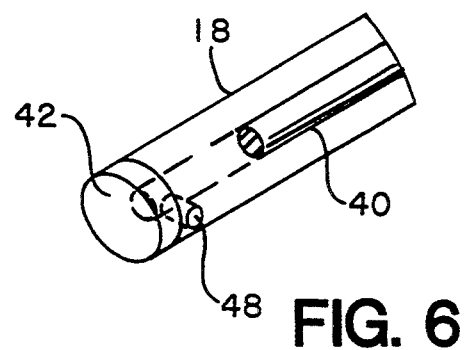

As yet a further alternative, as shown in FIG. 6, the mirror 42 may be permanently mounted to the wave guide end 26 and the sample 40 is drawn into the wave guide 18 via a lateral sample inlet bore 48 in the wave guide end 26.

Figure 7:
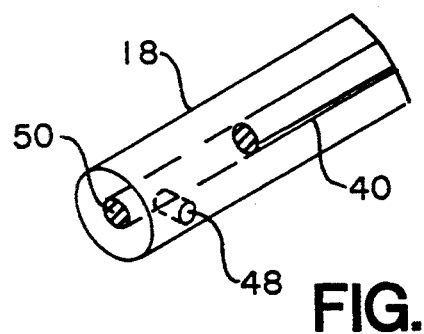

The mirror of the FIG. 7 embodiment is in the form of a polished wire 50 inserted within the wave guide end 26 to a point where it does not interfere with inlet bore 48.

As discussed above, optical fiber 20 acts as both a light transmitter and a light receiver. Coupler 34 performs the light splitting function between the transmitting and receiving channels. The fiber optic coupler 34 is referred to as a 1×2 coupler in the fiber optic art and typically has a splitting ratio of from 50/50 to 99/1 wherein the higher percentage light path is associated with the light analyzer.

While preferred embodiments have been described, various modifications and substitutions may be made thereto without departing from the spirit and scope of the invention. Accordingly, it is to be understood that the present invention has been described by way of illustration and not limitation.

What is claimed is:

1. Apparatus for measuring light absorption in small aqueous fluid samples comprising:
   a spectrophotometer cell in the form of a fluid core optical wave guide, said wave guide being of tubular construction and having first and second ends, said wave guide acting as a receiver for samples of liquid to be analyzed;
   means establishing fluid communication between the core region of said wave guide and the exterior of the wave guide, a liquid sample to be analyzed being drawn into and discharged from said wave guide via said fluid communication establishing means;
   a fiber optic piston inserted into said wave guide first end for imparting movement to the liquid sample to be analyzed;
   a source of analysis light;
   means for optically coupling said light source to said piston to thereby propogate light through a liquid sample which has been drawn into said wave guide via said fluid communication establishing means;
   light analysis means; and
   means for optically coupling said piston to said analysis means.

2. The apparatus of claim 1 wherein said wave guide comprises a rigid capillary tube having an internal surface for defining an interface with a liquid sample to be analyzed, said surface having an index of refraction which is less than 1.33.

3. The apparatus of claim 1 wherein said capillary tube is rigid and is formed from a fluoropolymer with a refractive index which is less than 1.33.

4. The apparatus of claim 1 wherein said wave guide further comprises reflector means sealing said wave guide second end whereby light directed into said sample at said wave guide first end is reflected back towards said wave guide first end.

5. The apparatus of claim 4 wherein a lateral sample inlet bore is provided in said wave guide adjacent to said second end thereof.

6. The apparatus of claim 1 wherein said means for coupling said light source to said piston includes light coupling and splitting means for directing light from said light source means to said fiber optic piston for transmittal to the aqueous fluid and for directing light received by said fiber optic piston to said means for coupling said piston to said piston to said analysis means.

7. The apparatus of claim 1 wherein said wave guide further comprises reflector means for selectively sealing said wave guide second end after a sample has been drawn into said wave guide whereby light directed into said sample at said wave guide first end is reflected back towards said wave guide first end.

8. The apparatus of claim 7 wherein said wave guide comprises a rigid capillary tube having an internal surface for defining an interface with a liquid sample to be analyzed, said surface having an index of refraction which is less than 1.33.

9. An apparatus for measuring light absorption in small aqueous fluid samples comprising:
a spectrophotometer cell in the form of a hollow axial core light wave guide having first and second ends, said wave guide being substantially rigid, said wave guide first end acting as a pipette tip through which aqueous fluid samples are drawn into said core sequentially for analysis and then expelled;
reflector means disposed in registration with said core adjacent said wave guide first end whereby light transmitted from said wave guide second end will travel through a sample disposed in said wave guide hollow axial core from said second end to said first end and be reflected back to said second end;
fiber optic plunger means in part inserted into said wave guide second end whereby contact between said fiber optic plunger means and a sample disposed in said wave guide hollow axial core will be established, said plunger means being optically coupled to a contacted sample in said core, analysis light being delivered to and received from the sample via said plunger means;
a light source optically coupled to said fiber optic plunger means; and
light analysis means optically coupled to said fiber optic plunger means, light from said light source delivered to said fiber optic plunger being propogated axially in two directions through the sample, light returned to said fiber optic plunger being delivered to said analysis means.

* * * * *